US012611270B2

(12) United States Patent
Zhou et al.

(10) Patent No.: US 12,611,270 B2
(45) Date of Patent: Apr. 28, 2026

(54) CONTROL OF AN ENDOSCOPE BY A SURGICAL ROBOT

(71) Applicant: Verb Surgical Inc., Santa Clara, CA (US)

(72) Inventors: Renbin Zhou, Santa Clara, CA (US); Seungkook Yun, Santa Clara, CA (US); Haoran Yu, Santa Clara, CA (US); Ellen Klingbeil, Santa Clara, CA (US); Apoorv Shrivastava, Santa Clara, CA (US)

(73) Assignee: AURIS HEALTH, INC., Santa Clara, CA (US)

( * ) Notice: Subject to any disclaimer, the term of this patent is extended or adjusted under 35 U.S.C. 154(b) by 1265 days.

(21) Appl. No.: 17/004,277

(22) Filed: Aug. 27, 2020

(65) Prior Publication Data

US 2022/0061936 A1 Mar. 3, 2022

(51) Int. Cl.
A61B 34/35 (2016.01)
A61B 34/00 (2016.01)
(Continued)

(52) U.S. Cl.
CPC .............. A61B 34/35 (2016.02); A61B 34/25 (2016.02); *A61B 2017/00199* (2013.01);
(Continued)

(58) Field of Classification Search
CPC . A61B 34/35; A61B 34/25; A61B 2034/2048; A61B 2034/2051;
(Continued)

(56) References Cited

U.S. PATENT DOCUMENTS

| | | | |
|---|---|---|---|
| 8,992,422 | B2 | 3/2015 | Spivey |
| 2007/0167679 | A1 | 7/2007 | Miyamoto et al. |

(Continued)

FOREIGN PATENT DOCUMENTS

| | | |
|---|---|---|
| CN | 102973321 A | 3/2013 |
| CN | 104758012 A | 7/2015 |

(Continued)

OTHER PUBLICATIONS

International Search Report and the Written Opinion for International Patent Application PCT/US2020/48138 mailed Nov. 20, 2020.

(Continued)

*Primary Examiner* — Aaron F Roane
(74) *Attorney, Agent, or Firm* — Lempia Summerfield Katz LLC

(57) ABSTRACT

An endoscope is controlled by a surgical robotic system. A user input with six degrees of freedom maps to control of an endoscope by a robotic arm having a fewer number of degrees of freedom. For example, untethered user interface devices control motion of an endoscope through a series of projections from user command, to endoscope motion, and to joint motion of the robotic arm. The projection from user command to endoscope motion may project a singular angular motion from three angular motions of the user interface devices. The projection may account for the remote center of motion and/or an angular orientation of the view of the endoscope relative to a shaft of the endoscope.

13 Claims, 5 Drawing Sheets

(51) Int. Cl.

| | |
|---|---|
| A61B 17/00 | (2006.01) |
| A61B 18/00 | (2006.01) |
| A61B 18/12 | (2006.01) |
| A61B 34/20 | (2016.01) |
| A61B 34/30 | (2016.01) |

(52) U.S. Cl.

CPC .............. *A61B 2017/00973* (2013.01); *A61B 2018/00595* (2013.01); *A61B 2018/1253* (2013.01); *A61B 2018/126* (2013.01); *A61B 2034/2048* (2016.02); *A61B 2034/2051* (2016.02); *A61B 2034/2055* (2016.02); *A61B 2034/301* (2016.02); *A61B 2034/742* (2016.02)

(58) Field of Classification Search

CPC ...... A61B 2034/2055; A61B 2034/301; A61B 2034/742; A61B 2017/00199; A61B 2017/00973; A61B 2018/00595; A61B 2018/1253; A61B 2018/126

USPC .......................................................... 606/1

See application file for complete search history.

(56) References Cited

U.S. PATENT DOCUMENTS

| 2012/0039681 | A1 | 2/2012 | Ishida |
| 2012/0316681 | A1 | 12/2012 | Hagn |
| 2014/0039681 | A1 | 2/2014 | Bowling |
| 2014/0316681 | A1 | 10/2014 | Whitney et al. |
| 2017/0020615 | A1 | 1/2017 | Koenig |
| 2017/0095295 | A1* | 4/2017 | Overmyer ................ B25J 13/02 |
| 2018/0036088 | A1* | 2/2018 | Kilroy ................... A61B 34/74 |

| 2019/0000578 | A1 | 1/2019 | Yu |
| 2019/0125462 | A1* | 5/2019 | Peine .................... A61B 34/74 |
| 2019/0175286 | A1 | 6/2019 | Zhou |
| 2019/0176334 | A1 | 6/2019 | Zhou |
| 2019/0201142 | A1 | 7/2019 | Shelton, IV et al. |
| 2019/0320874 | A1 | 10/2019 | Yu |
| 2020/0054401 | A1 | 2/2020 | Yu |
| 2020/0054403 | A1 | 2/2020 | Zhou |
| 2020/0138524 | A1 | 5/2020 | Brunelli et al. |
| 2020/0289205 | A1 | 9/2020 | Scheib et al. |
| 2020/0289230 | A1* | 9/2020 | Denlinger ............. A61B 34/74 |

FOREIGN PATENT DOCUMENTS

| CN | 104758060 A | 7/2015 |
| CN | 106890025 A | 6/2017 |
| WO | 2014028558 A1 | 2/2014 |
| WO | 2018013965 A1 | 1/2018 |

OTHER PUBLICATIONS

De Moura, Diogo Turiani Hourneaux, Hiroyuki Aihara, and Christopher C. Thompson. "Robotic-assisted surgical endoscopy: a new era for endoluminal therapies." VideoGIE 4.9 (2019): 399.

Mettler, L., M. Ibrahim, and W. Jonat. "One year of experience working with the aid of a robotic assistant (the voice-controlled optic holder AESOP) in gynaecological endoscopic surgery." Human reproduction (Oxford, England) 13.10 (1998): 2748-2750.

European Search Report for European Application No. 20951779.6-1113 mailed Mar. 28, 2024.

Chinese Office Action for Chinese App. No. 202080103502.0 mailed Mar. 14, 2025, with English translation.

* cited by examiner

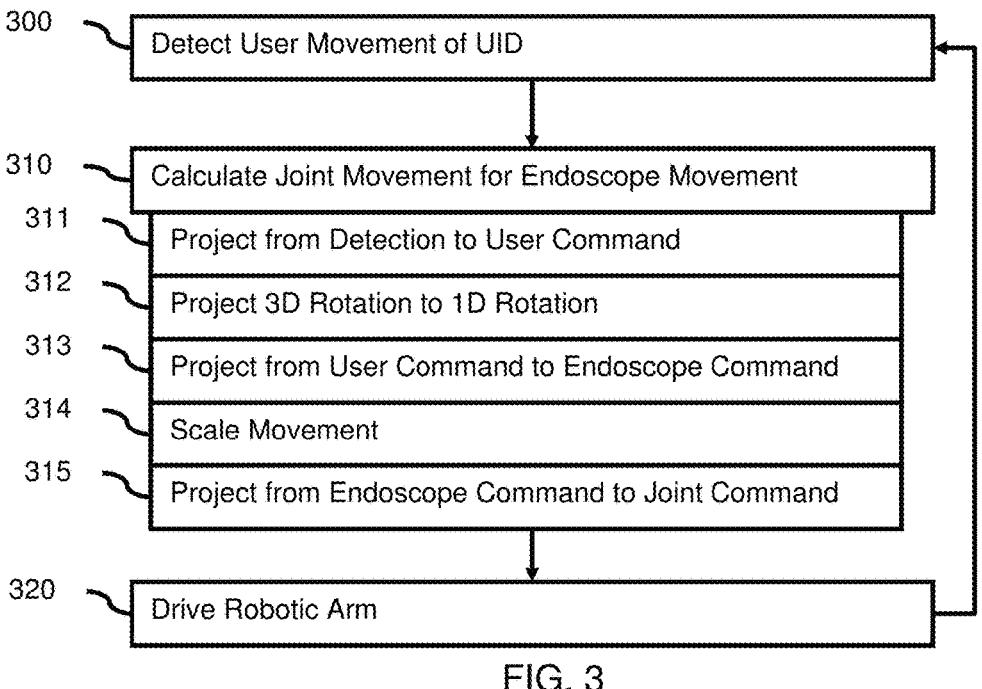

300  Detect User Movement of UID

310  Calculate Joint Movement for Endoscope Movement

311  Project from Detection to User Command

312  Project 3D Rotation to 1D Rotation

313  Project from User Command to Endoscope Command

314  Scale Movement

315  Project from Endoscope Command to Joint Command

320  Drive Robotic Arm

FIG. 3

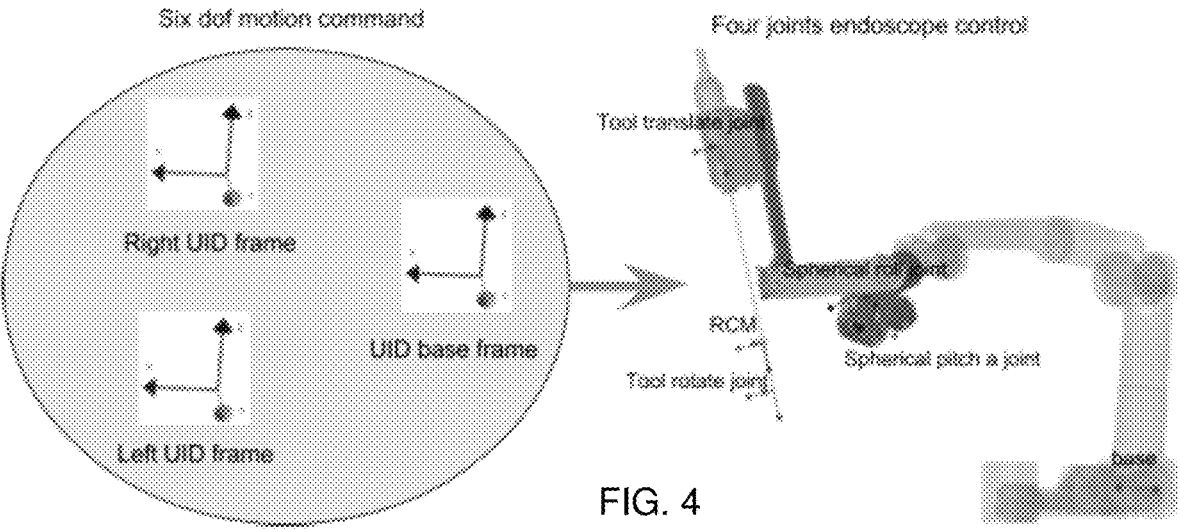

Six dof motion command

Right UID frame

UID base frame

Left UID frame

Four joints endoscope control

Tool trans

RCM

Tool rotate joint

Spherical pitch a joint

FIG. 4

CONTROL OF AN ENDOSCOPE BY A SURGICAL ROBOT

BACKGROUND

The present embodiments relate to robotic systems for minimally invasive surgery (MIS). MIS may be performed with robotic systems that include one or more robotic manipulators for manipulating surgical tools based on commands from a remote operator. A robotic manipulator may, for example, support at its distal end various surgical instruments and devices, including an endoscope. Using the robotic system, the surgeon controls the robotic manipulator with the endoscope in teleoperation during MIS.

An endoscope in robotics MIS provides a surgical site view and a global reference. During teleoperation, the hand and/or wrist motion of the surgeon is captured by a master control device. The endoscope motion follows the captured motion. The robotic arm may have limited movement, especially as compared to the greater freedom of the master control device. An ambiguity between motion of the master control device and motion of the endoscope results.

SUMMARY

By way of introduction, the preferred embodiments described below include methods, systems, instructions, and computer readable media for control of an endoscope by a surgical robotic system. A user input with six degrees of freedom maps to control of an endoscope by a robotic arm having a fewer number of degrees of freedom. For example, untethered user interface devices control motion of an endoscope through a series of projections from user command, to endoscope motion, and to joint motion of the robotic arm. The projection from user command to endoscope motion may project a singular angular motion from three angular motions of the user interface devices. The projection may account for the remote center of motion and/or an angular orientation of the view of the endoscope relative to a shaft of the endoscope.

In a first aspect, a method is provided for control of an endoscope by a surgical robotic system. Movement by a handheld user input device having six degrees of freedom is detected. The movement by the handheld user input device is mapped to movement of the endoscope coupled to a robotic manipulator of the surgical robotic system. The movements of one or more joints of the robotic manipulated are calculated to facilitate the movement of the endoscope. The one or more joints are driven according to the calculated movements.

In a second aspect, a method is provided for control of an endoscope by a surgical robotic system. Input translation and rotation about three axes is sensed. The input rotation about the three axes is projected to rotation about a single axis for the endoscope mounted to a robotic arm. The robotic arm is controlled to move the endoscope based on the sensed input translation and the protected rotation about a single axis.

In a third aspect, a surgical robotic system is provided. An endoscope is coupled to a robotic manipulator. A controller is configured to translate displacements of one or more user interface devices to a scaled displacement of the endoscope. The translation reduces a first degree of freedom (DoF) of rotations of the user interface devices to a fewer second number of DoF of rotations of the endoscope.

The present invention is defined by the following claims, and nothing in this section should be taken as a limitation on those claims. Any teaching for one type of claim (e.g., method) may be applicable to another type of claim (e.g., computer readable storage medium or system). Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 3 is a flow chart diagram of one embodiment of a method for control of an endoscope by a surgical robotic system;

FIG. 4 illustrates an example relationship between the six degrees of motion of the user interface and four degrees of freedom of movement of the endoscope by the robotic manipulator during teleoperation;

DETAILED DESCRIPTION OF THE DRAWINGS AND PRESENTLY PREFERRED EMBODIMENTS

Endoscope control is provided in robotics MIS. One or more UIDs have six degree of freedom, and the robot arm has fewer (e.g., four) joints and corresponding degrees of freedom during MIS. The motion space of one or more user interface devices (UIDs) is incompatible with the arm motion space of the robotic arm, so the user device motion is projected to the endoscope motion space. User motion commands (UMC) are generated from UID motions. The UMCs are mapped to endoscope motion commands (EMC). The projection is achieved by projecting the angular motion command but passing through the linear motion commands without any projection, resulting in the projected UMC. The EMCs are mapped to arm joint motion commands (JMC).

In further embodiments, the endoscope motion is constrained by the mechanical or virtual remote center of motion (RCM) of the robotic arm during MIS. The UMCs are further projected into the RCM motion space, resulting in EMCs constrained by RCM. The EMC is mapped to the arm JMC through inverse kinematics. Additionally, to avoid fast arm motion when the endoscope end is close to the RCM, a dynamic scaling technique is used.

Figure 1:
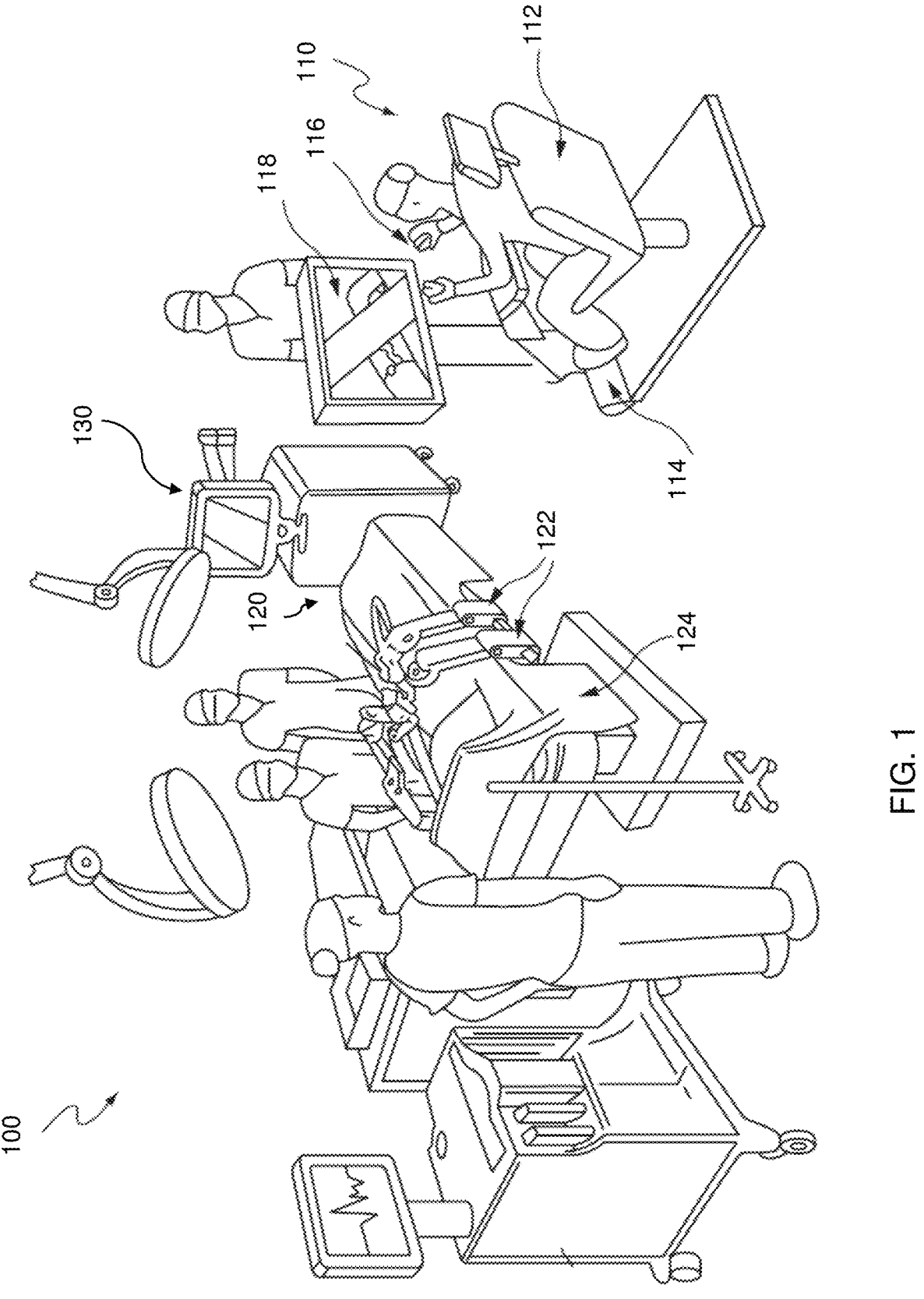
FIG. 1 is an illustration of one embodiment of an operating room environment with a surgical robotic system according to one embodiment.
Figure 2:
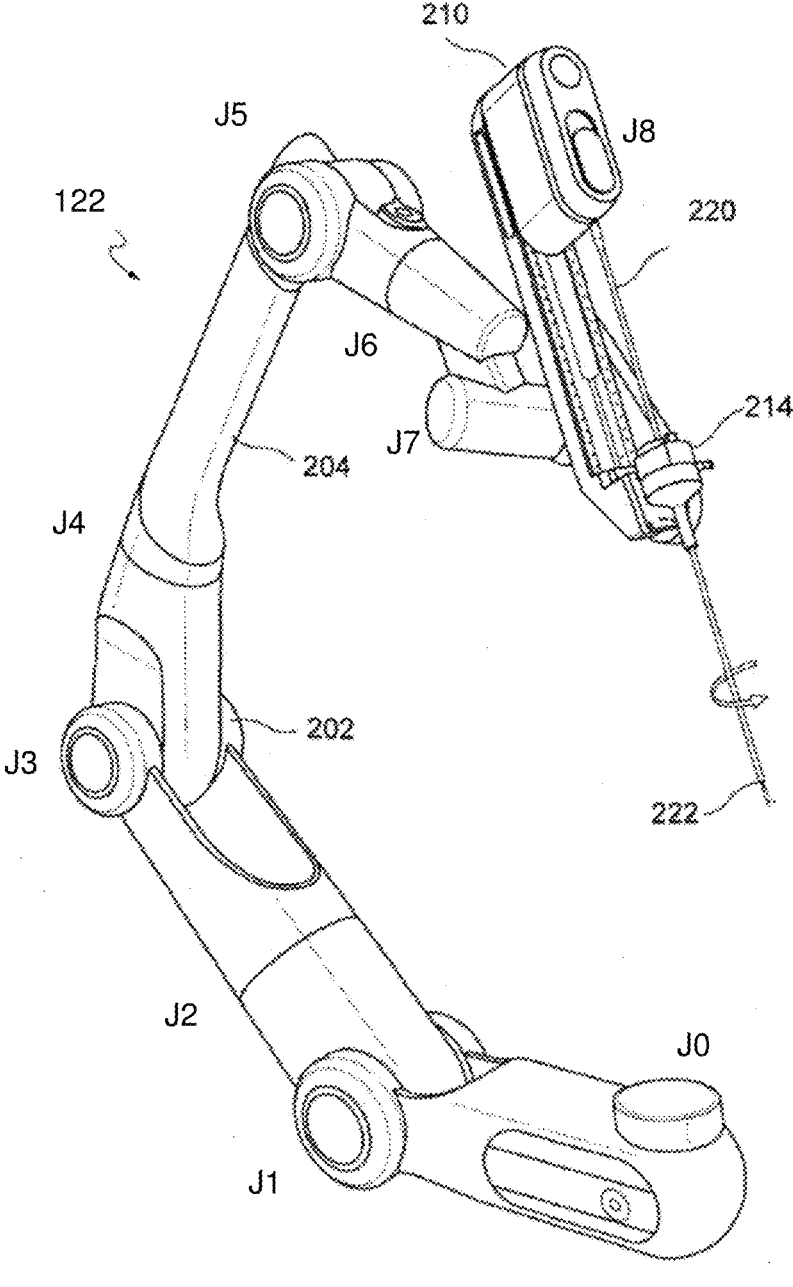
FIG. 2 illustrates an example surgical robot arm and surgical tool.

FIGS. 1 and 2 show an example surgical robotic system. The approaches for endoscope control are discussed below in reference to this example system. Other surgical robotic systems and surgical robots or non-surgical robotic systems and robots may use the approaches.

FIGS. 3-7 are directed to endoscope control, including reduction in degrees of freedom of the UIDs relative to the degrees of freedom of the robotic arm. FIG. 8 is directed to a system for robotic control of an endoscope or similar tool with limited degrees of freedom.

FIG. 1 is a diagram illustrating an example operating room environment with a surgical robotic system 100 for which commands from the user are converted into motion of the surgical robotic manipulators 122 with projection to reduce the number of degrees of freedom, account of the RCM, and/or scaling. The surgical robotic system 100 includes a user console 110, a control tower 130, and a surgical robot 120 having one or more surgical robotic manipulators (arms) 122 mounted on a surgical platform 124 (e.g., a table or a bed etc.), where surgical tools with end effectors are attached to the distal ends of the robotic manipulators 122 for executing a surgical procedure. Additional, different, or fewer components may be provided, such as combining the control tower 130 with the console 110 or surgical robot 120. The robotic manipulators 122 are shown as table-mounted, but in other configurations, the robotic manipulators 122 may be mounted in a cart, a ceiling, a sidewall, or other suitable support surfaces.

Generally, a user, such as a surgeon or other operator, may be seated at the user console 110 to remotely manipulate the robotic manipulators 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may include a seat 112, pedals 114, one or more handheld user interface devices (UIDs) 116, and an open display 118 configured to display, for example, a view of the surgical site inside a patient and graphic user interface. As shown in the exemplary user console 110, a surgeon sitting in the seat 112 and viewing the open display 118 may manipulate the pedals 114 and/or handheld UIDs 116 to remotely and directly control the robotic arms 122 and/or surgical instruments mounted to the distal ends of the arms 122. The user inputs commands for the movement of the surgical manipulators 122 and/or end effectors. This user control determines position, the rate of movement, and the change in rate of movement of the robotic manipulators 122. The rate and change in rate result in dynamic torque expected to be provided by the robotic manipulators 122. The surgeon sitting in the seat 112 may view and interact with the display 118 to input commands for movement in teleoperation of the robotic manipulators 122 and/or surgical instruments (e.g., endoscope) in the surgery.

In some variations, a user may also operate the surgical robotic system 100 in an "over the bed" (OTB) mode, in which the user is at the patient's side and simultaneously manipulating a robotically-driven tool/end effector attached thereto (e.g., with a handheld UID 116 held in one hand) and a manual laparoscopic tool. For example, the user's left hand may be manipulating a handheld UID 116 to control a robotic surgical component while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or UIDs 116 to manipulate various end effectors and/or imaging systems to perform the surgery using teleoperation. The movements may be surgeon, patient, and/or situation specific, so may vary. Manual assistance may also be provided at the procedure table by sterile-gowned personnel, who may perform tasks including but not limited to, retracting tissues or performing manual repositioning or tool exchange involving one or more robotic manipulators 122. Some surgical tasks, such as retracting, suturing, or other tissue manipulation, may instead be performed by one or more robotic manipulators 122 (e.g., third or fourth arms). Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input commands from the user console 110 to robotic control commands and transmit the control commands to the surgical robot 120. The control tower 130 and/or user console 110 performs projection and/or inverse kinematics. The control tower 130 may also transmit status and feedback from the robot 120 back to the user console 110. The connections between the surgical robot 120, the user console 110, and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform preoperative setup. During the preoperative setup, the main components of the surgical robotic system (e.g., table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms 122 from their stowed position for sterile draping. After draping, the arms 122 can be partially retracted until needed for use. A number of conventional laparoscopic steps may need to be performed including cannula placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other cannulas. After insufflation, if required, manual instruments can be inserted through the sleeve to perform any laparoscopic steps by hand.

Next, the surgical team may position the robotic arms 122 over the patient and attach each arm 122 to a corresponding sleeve (e.g., cannula). The surgical robotic system 100 has the capability to uniquely identify each tool (endoscope and surgical instruments) upon attachment and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery as teleoperation using the tools controlled by one or more (e.g., two) master UIDs 116 and one or more foot pedals 114. The system translates the surgeon's hand, wrist, and finger movements through the master UIDs 116 into precise real-time movements of the surgical tools. Therefore, in direct teleoperation, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

FIG. 2 is a schematic diagram illustrating one exemplary design of a robotic manipulator 122, a tool drive 210, and a connector loaded with a robotic surgical tool (e.g., an endoscope 220), in accordance with aspects of the subject technology. As shown in FIG. 2, the example surgical robotic manipulator 122 may include a plurality of links (e.g., a link 202) and a plurality of actuated joint modules (e.g., a joint 204, see also joints J1-8) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 122. The tool drive 210 may include a cannula 214 coupled to its end to receive and guide a surgical instrument (e.g., endoscope 220) or end effector 222. The surgical instrument (or "tool") is an endoscope 220 and may include an end effector 222 at the distal end of the tool. The plurality of the joint modules of the robotic manipulator 122 can be actuated to position and orient the tool drive 210, which actuates or moves the end effector 222 for robotic surgeries. The end effector 222 is at a tool shaft end, such as being a lens of an endoscope on a shaft.

In the example of FIG. 2, the joint J0 is a table pivot joint and resides under the surgical table top. Joint J0 is nominally held in place during surgery. Joints J1 to J5 form a setup or Cartesian arm and are nominally held in place during surgery, so do not contribute to motion during surgical teleoperation. Joints J6 and J7 form a spherical arm that may actively move during surgery or teleoperation. Joint J8 translates the tool 220, such as the end effector 222, as part of a tool driver. Joint J8 may actively move during surgery, translating the end effector along the axis of the shaft. Joints J6-8 actively position a tool shaft end (i.e., end effector 222) during surgery while maintaining an entry point into the patient at a fixed or stable location (i.e., RCM) to avoid stress on the skin of the patient. During set-up, any of the joints J0-J8 may move. During surgery, the joints J6-8 may move subject to hardware or safety limitations on position, velocity, acceleration, and/or torque. The surgical tool as an endoscope 220 may be rotated about the longitudinal shaft or other axis, which rotation may be the only degree of freedom of the endoscope. Any number of degrees of freedom may be provided, such as the three degrees from the joints J6-8 and one degrees from the endoscope 220 (i.e., four degrees of freedom with three from the joints J6-8 and one from the rotation of the endoscope).

FIG. 3 is a flow chart diagram of one embodiment of a method for control of an endoscope 220 by the surgical robotic system 100. Movement of the UIDs 116 is mapped to a lesser number of angular motions as part of projecting surgeon motion to joint motion.

The method of FIG. 3 is implemented by a control processor, such as the control tower 130, computer, workstation, sever, or another processor. Any computer of the surgical robotic system 100 may be used. A user interface provides the movement commands from the user received in act 300. The control processor (e.g., controller) maps the UID movements to the robotic manipulator movement in act 310. The robotic arm 122 and/or endoscope 220 are moved using the instructions or control from the control processor in act 320. Other devices may perform and/or be used in any of the acts.

The acts are performed in the order shown or other orders. For example, act 300 is performed after any of the other acts. As another example, act 320 is performed before or after any of the acts, such as in an ongoing teleoperation.

Additional, different, or fewer acts may be used. For example, any of the projections or scaling of acts 311-315 is performed alone or in combination with fewer than all of the acts. In another example, acts for initially positioning the endoscope 220 in the patient, planning surgery, and/or removing the endoscope 220 from the patient may be provided.

In act 300, a sensor detects input movement of one or more UIDs 116. Magnetic position sensing, optical sensing, electric field sensing, or other sensing is performed to wirelessly detect movement of the UIDs 116, such as movement by the user. Gyroscopes, accelerometers, and/or other sensors on or in the UIDs 116 may detect input movement of the UIDs 116 (e.g., sense the orientation and/or translation of the UIDs 116).

The UIDs 116 are handheld, such as being objects of any shape with or without buttons, knobs, and/or joysticks. The UIDs 116 are untethered, such as not being physically connected to other devices (i.e., no mechanical linkage and no cable). In other embodiments, a cable is provided for communication. As the user translates and/or rotates the UIDs 116, this motion or change in location and/or orientation (i.e., change in pose or position) is detected by a sensor, providing a base frame of reference (i.e., UID 116 relative to the remotely positioned sensor).

Since the UIDs 116 are handheld, the UIDs 116 each have six degrees of freedom. Three degrees of translation along orthogonal spatial axes (x, y, z) and three degrees of rotation about the three spatial axes, providing roll, pitch, and yaw. The translation and/or rotation about these three axes are sensed, providing pose or position. One or both UIDs are sensed while being held by the operator in their hand and while physically unconnected to other devices.

The position or change in position (e.g., linear and rotational motion) are sensed. The sensing samples at any frequency, such as every 0.1 seconds. The position or change in position is sampled for one or both UIDs 116.

In act 310, the controller calculates movements of one or more joints of the robotic manipulator to facilitate movement of the endoscope 220. The controller maps the movement by the handheld user input device (e.g., UID 116) to movement of the endoscope 220 held by a robotic manipulator 122 of the surgical robotic system 100. The mapping relates the movement of the UID or UIDs 116 to joint motion to cause the endoscope 220 to move.

FIG. 3 shows five acts 311-315 involved in the calculation to map. Additional, different, or fewer acts may be used. For example, act 314 is not provided. As another example, act 312 is an aspect of the mapping that may be combined with or be part of another of the acts, such as the projection of act 311. Any given projection may be sub-divided into multiple acts, such as the projection of act 313 including translating the user commands to arm motion, the arm motion to an RCM frame, and then the RCM frame to the motion of the endoscope 220. Other mapping to translate from the sensed UID motion to the motion of the joints may be used.

Figure 5:
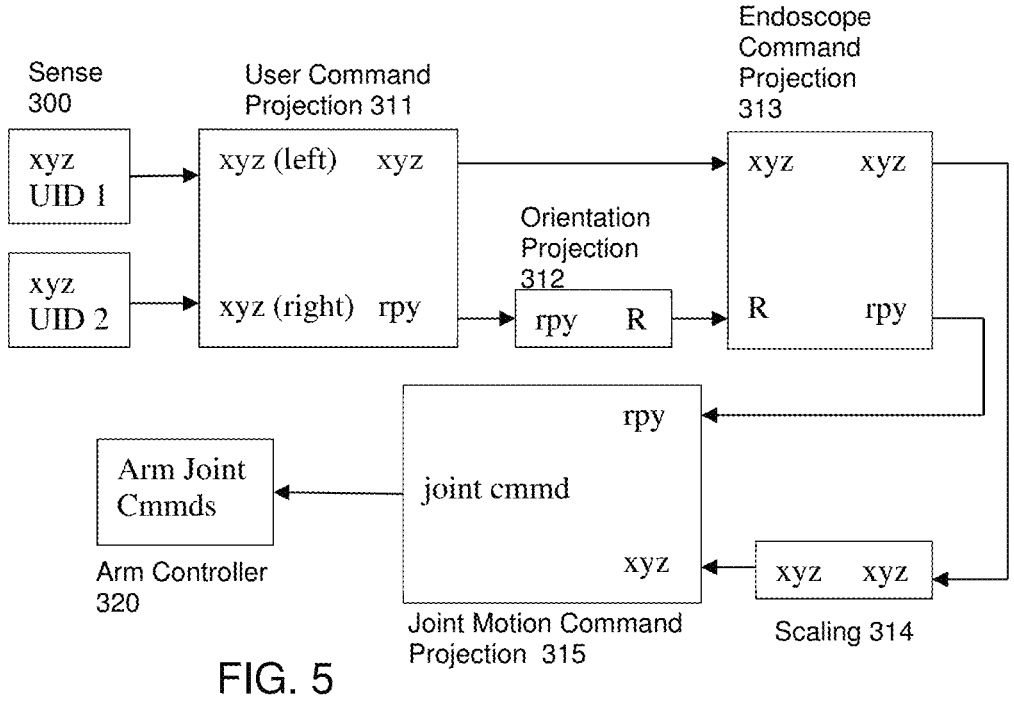
FIG. 5 illustrates an example projection sequence for mapping user input motion to joint motion of the robotic manipulator.

FIG. 5 represents the sequence of acts 311-315. This representation is a flow chart and/or software modules for mapping from the sensing of act 300 to the movement of the joints (e.g., J6-8) of the robotic arm 122.

In act 311, the controller projects from the sensing to a user motion command for the endoscope. The motion or position of the UIDs 116 is translated to user commands. The change input by the user through the UIDs 116 is interpreted from the sensed motion and/or position.

One UID 116 may be used to control motion or position of the endoscope. Alternatively, a combination of two UIDs 116 are used to control motion or position of the endoscope. For example, the coordinated movement of both UIDs 116 controls the motion, such as using relative motion to derive the user input motion in six degrees of freedom. The change in position and/or orientation of two handheld user interface objects are detected where the movement at a virtual center point between the two handheld user interface objects is used as the entered movement for controlling the endoscope. The user holds a UID 116 in each hand (left and right) (see FIG. 1), where the motion of both UIDs 116 is sensed to determine the coordinated motion being entered by the surgeon. The user translation and rotation about the three axes corresponding to six degrees of freedom at a center point between the UIDs 116 is detected.

In preparation for teleoperation, the user sits down at the surgeon console 110. After positioning of the robotic manipulator 122 for teleoperation, one or more joints are locked in place with a RCM at the patient skin or incision entry point. For example, joints J0-J5 (see FIG. 2) are locked. The locking is by a brake and/or avoiding energizing the motors for the joints. These joints remain locked during teleoperation. Any of joints J0-J5 may be unlocked and moved to change the RCM.

During teleoperation, the user enters commands to move the robotic manipulator 122 and/or endoscope 220. The commands are for motion. Different commands may be provided for different movements. The commands may be for movement of the end effector 222. These commands may not be for movement of particular joints. The control processor converts the movement commands to controls of particular joints of the robotic manipulator 122 and/or surgical tool 220.

The control processor receives a user command to move the robotic manipulator 122 or endoscope 220 of the robotic manipulator 122 prior to or during the teleoperation on a patient. The user input is received from the user console 110, such as the UIDs 116, via wireless or wired interface by the control processor. In other embodiments, the user commands are received by loading from memory or transmission over a computer network.

In one embodiment, user commands are generated based on a reference frame or coordinate system. As soon as entering teleoperation, the location (x,y,z) of both UIDs 116 are used to create the reference frame. The center point between the two UIDs 116 is determined. This center point is represented as:

$$\vec{O} = \frac{1}{2}\left(\vec{O}_l + \vec{O}_r\right) \tag{1}$$

Where, $\vec{O} = [x_0, y_0, z_0]$—origin vector of the reference frame, $\vec{O}_l = [x_{l0}, y_{l0}, z_{l0}]$—position vector of the left UID, and $\vec{O}_r = [x_{r0}, y_{r0}, z_{r0}]$—position vector of the right UID.

The center point is used as the origin with the axes of the base frame being assigned about this center point.

The reference frame about this center point may be established statically or dynamically. To create the reference frame statically, the center point between the two UID positions is used as the origin, and the axes (x, y, z) of the reference frame is the same as the base frame of the UIDs 116. The x, y, z axes of the sensor of the UIDs 116 is used.

To create the reference frame dynamically, the center point is used as the origin, but the y-axis is defined from the right UID location to that of the left UID location, or vice versa. The y-axis is given by the relative locations of the UIDs 116. The x-axis is perpendicular to the y-axis and pointing toward the base frame (i.e., from the center point to the sensor or origin of the base. The z-axis forms a right-hand coordinate system with x and y-axis. This dynamic creation, allowing some control of the origin and directions by the user, may be represented as:

$$\vec{z}_{axis} = [0.0, 0.0, 1.0] \tag{2}$$

$$\vec{y}_{axis} = \frac{o_l - o_r}{\|o_l - o_r\|},$$

$$\vec{x}_{axis} = \vec{y}_{axis} \times \vec{z}_{axis}$$

Where, $\vec{O}_l = [x_{l0}, y_{l0}, z_{l0}]$—position vector of the left UID, and $\vec{O}_r = [x_{r0}, y_{r0}, z_{r0}]$—position vector of the right UID.

In both static and dynamic generation of the reference coordinate system, a multiple location sample average may be used to reduce the random noise of the UID location. The reference frame is created once when first entering teleoperation, and remains the same until the user exits teleoperation.

For detecting motion, the sensor detects the position (linear and angular pose) of the UIDs at different sample times. Two consecutive UIDs center point positions relative to or in the reference frame are used as the user motion command (UMC). The change in position relative to the reference axes (e.g., translation and/or rotation about three reference axes) is detected. This change in position or motion vector with six degrees of freedom is represented as:

$$\vec{\Delta}_u = \vec{O}_t - \vec{O}_{t-1} \tag{3}$$

Where, $\vec{\Delta}_u$—user motion command vector $\vec{O}_t$—center position vector of two UIDs at current time (t)

$\vec{O}_{t-1}$—center position vector of two UIDS at previous time (t−1)

$$R_u = R_t * (R_{t-1})^T \qquad (4)$$

Where, $R_u$—rotation matrix (3×3) of user command $R_t$—rotation (3×3) matrix of UIDs at current time (t)

$R_{t-1}$—rotation matrix (3×) of UIDs at previous time step (t−1).

The center point translation along three or fewer spatial axes and the rotation about the three spatial axes is detected, providing the user motion command vector in translation and rotation. For example, the user moves their hands forward for translation while bending their wrists downward to provide for moving the endoscope while rotating the endoscope. The translations and/or rotations of the center point about all three axes may be detected.

In act 312, the controller projects the input rotation about the three axes to rotation about a single axis for the endoscope mounted to the robotic arm. The degrees of freedom of the UIDs 116 (e.g., six degrees of freedom including three linear translation and three rotation) is reduced to match the degrees of freedom of the robotic manipulator 122. In the example of FIG. 4, the six degrees of freedom are reduced to four degrees of freedom of the arm provided by joints J6-8 and rotation of the endoscope 220. In other examples, the reduction is from six to five or six to three.

The projection in this embodiment provides reduction in the degrees of freedom for rotation, such as three degrees to one. In other embodiments, part or all of the reduction is in translation degrees of freedom.

FIGS. 3 and 5 shows the rejection as part of or after the projection to user commands and/or before the projection from user commands to endoscope commands. The reduction takes place in the user command space. In other embodiments, the reduction occurs in other spaces or parts of the mapping, such as in the detection space of act 311, the endoscope command space (e.g., after act 313), in the scaled space (e.g., after act 314), or in the joint command space (e.g., after act 315).

In the examples of FIG. 5, the roll, pitch, and yaw of the user commands is projected to provide one rotation (e.g., roll) without the other rotations (e.g., yaw and pitch). This orientation projection drops, removes, or does not use sensed yaw and pitch. Alternatively, the rotations in three degrees of freedom are changed into a single rotation about one axis. Any function relating the rotation vector to a fewer (e.g., singular) number of rotations may be used. The projection in orientation provides a rotation R or rotation vector $\vec{R}$. In the example of FIG. 4, the rotation R is for rotation of the endoscope about the shaft or in the arm space.

The linear translations are not projected or are projected as unchanged. The linear translations xyz are passed for generating the endoscope commands in act 313. The projected orientation, such as the roll or rotation R, is passed for generating the endoscope commands in act 313.

In one embodiment, the orientation of the user motion commands is projected into only the roll space in the reference frame. The yaw and pitch are set to zero. The projection uses the roll and does not use the yaw and pitch in the reference frame established in the sensing and generation of user commands of act 311. The orientation projection of act 312 may be represented as:

$$[r,p,y] = \text{Convert\_To\_Euler\_Angle}(R_u),$$

$$R_u = \text{Convert\_To\_Rotation}([r,0.0,0.0]) \qquad (5)$$

Where, $R_u$—3×3 rotation matrix of user command r—roll angle about $\vec{x}_{axis}$ p—pitch angle about $\vec{y}_{axis}$ y—yaw angle about $\hat{z}_{axis}$.

Equation 5 shows the conversion to a single Euler angle, $R_u$, by dropping the pitch and yaw, and an inverse conversion back to the reference frame. The inverse has roll with zero for yaw and pitch. The projection may just remove the pitch and yaw where the reference frame is to be maintained and a single rotation about an axis of the reference frame is used.

Figure 6:
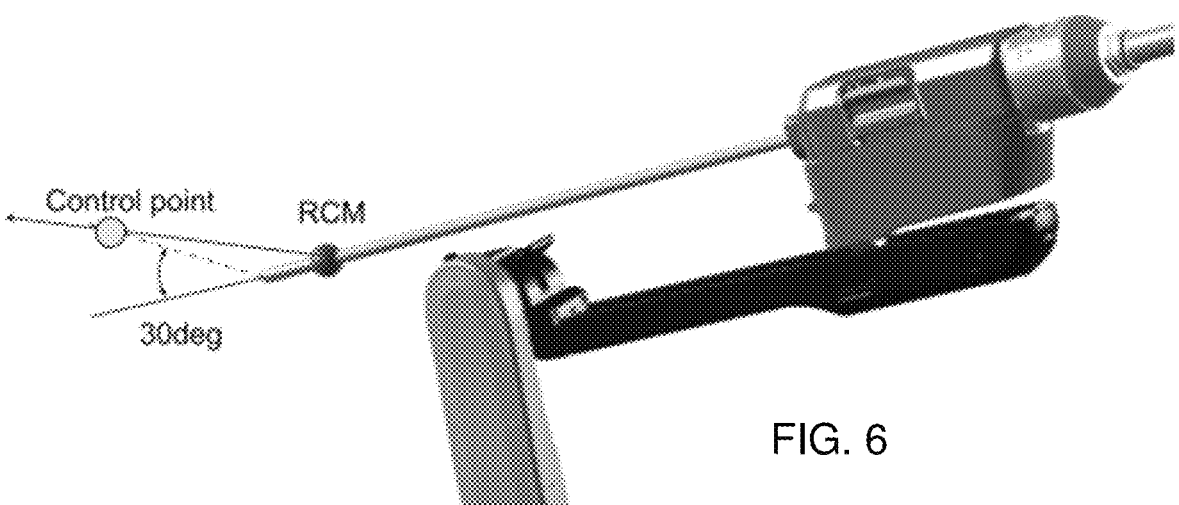
FIG. 6 illustrates an example endoscope with an angled field of view.

The endoscope 220 may have a view direction centered along the longitudinal axis or shaft of the endoscope 220. In other embodiments, the view direction is offset at a non-zero angle from the shaft. FIG. 6 shows an example with a 30-degree offset in angle, but smaller or larger angle offsets may be used. The roll or rotation maintained in the orientation projection of act 312 is about an axis from a remote center of motion of the robotic manipulator to a control point based on the non-zero angle of a viewer of the endoscope 220. The rotation (roll) axis is defined by a line passing through the RCM and a user defined point (e.g., image center) on the endoscope view axis. This point serves as a control point, such that as the user rotates the endoscope, the image center point remains stationary. The user is inputting commands relative to the view on the screen, so the rotation is of that view. The angular motion is mapped about an axis from the remote center of motion of the robotic manipulator 122 to a control point based on a non-zero angle of a viewer of the endoscope 220.

In act 313, the controller projects the user motion commands to endoscope commands. The user motion commands are to control the endoscope 220. The projection indicates the motion of the end effector, ee, or tip of the endoscope 220.

Since the robotic manipulator 122 moves the endoscope 220 and is constrained by the remote center of motion, the projection to the endoscope command space accounts for the remote center of motion. The end effector of the endoscope 220 is moved in a way constrained by the remote center of motion. The projection to the endoscope command space is for motion of the endoscope 220 where a position along the shaft of the endoscope 220 is to be maintained stationary.

The projection to the endoscope command space converts or translates the user motion commands for the endoscope 220 to a remote center of motion frame of the robotic manipulator 122. In one approach, the projection defines the motion in a frame of reference of the robotic manipulator 122. The motion is converted to a remote center of motion frame. This conversion results in the rotation with fewer than three degrees of freedom (e.g., rotation about a single axis from the orientation projection of act 312) being rotation about three axes. Since the remote center of motion is stationary, the linear translation and rotation of the endoscope 220 of the user commands may cause the end effector to translate and rotate in six degrees of freedom. The projection to the endoscope command space constrained by the remote center of motion provides rotation about three axes. The motion in the remote center of motion frame is then converted back from the remote center of motion frame to the arm frame with added rotation from the remote center of motion frame.

The yaw and pitch components are included. In one embodiment, the yaw and pitch are removed from the user command space. The yaw and pitch are added back in the endoscope command space but are relative to the remote center of motion instead of the reference frame established in the user command projection of act 311.

The projections provide for projecting the movement by the handheld user input device (e.g., UID 116) to a remote center of motion reference frame of the robotic manipulator 122. The sequence of projections of acts 311-313 and/or of act 313 discussed above or a different projection or projection sequence may be used to convert the detected movement of the UIDs 116 to endoscope motion constrained by the remote center of motion.

In one embodiment, the user motion commands are projected to the remote center of motion frame of the robotic manipulator 122, creating endoscope commands. The user motion commands are converted into a robotic arm space based on motion of the end effector of the endoscope 220, as represented by:

$$\substack{arm\\ee}\vec{O}_t = \substack{arm\\ee}\vec{O}_{t-1} + \vec{\Delta}_u \tag{6}$$

$$\substack{arm\\ee}R_t = \substack{arm\\rcm}R_t * R_u$$

Where, $$\substack{arm\\ee}\vec{O}_t$$

—Endoscope end position vector (1×3) in arm base frame at current time (t)

$$\substack{arm\\ee}\vec{O}_{t-1}$$

—Endoscope end position vector (1×3) in arm frame at previous time (t–1)

$$\substack{arm\\ee}R$$

—Endoscope end frame rotation matrix (1×3) in arm frame $$\substack{arm\\rcm}R$$

—Endoscope RCM frame rotation matrix (3×3) in arm frame.

$R_u$—rotation matrix (3×3) from user command

The location in three-dimensional space is determined from the last position and the change in linear translation from the user commands. The rotation of the end effector is provided by the rotation from the user command convolved with or multiplied by the rotation of the end effector as constrained by the remote center of motion frame.

The translation and rotation in the arm space are constrained by the remote center of motion. The projection into the remote center of motion frame is represented as:

$$\left[\substack{rcm\\ee}\vec{O}_t, 1.0\right]^T = \substack{arm\\rcm}T_t * \left[\substack{arm\\ee}\vec{O}_t, 1.0\right]^T \tag{7}$$

-continued $$\left[\substack{rcm\\ee}\vec{O}_{t-1}, 1.0\right]^T = \substack{rcm\\arm}T_{t-1} * \left[\substack{arm\\ee}\vec{O}_{t-1}, 1.0\right]^T$$

$$\substack{rcm\\ee}\vec{O}_{t-1} = \left(\substack{rcm\\ee}\vec{O}_{t-1}\right) * \frac{\|\substack{rcm\\ee}\vec{O}_t\|}{\|\substack{rcm\\ee}\vec{O}_{t-1}\|}$$

$$R = RodriquesRotation\left(\substack{rcm\\ee}\vec{O}_{t-1}, \substack{rcm\\ee}\vec{O}_t\right)$$

Where, $$\substack{rcm\\ee}\vec{O}_t$$

—Endoscope end position vector (1×3) in RCM frame at current time (t)

$$\substack{rcm\\ee}\vec{O}_{t-1}$$

—Endoscope end position vector (1×3) in RCM frame at previous time (t–1)

$$\substack{rcm\\arm}T_t$$

—transformation matrix (4×4) from an arm frame to RCM frame

R—rotation matrix (3×3) and $$\substack{rcm\\ee}\vec{O}_t = R * \left(\substack{rcm\\ee}\vec{O}_{t-1}\right).$$

A translation is given in three dimensions for the end effector of the endoscope 220. To define this translation in the context of a four-dimensional matrix, a 1.0 term is added. Rotation about three dimensions constrained by the remote center of motion is provided.

Once the constraint provided by the remote center of motion frame is added as shown in equation 7, the resulting translation and rotation are converted back to the arm frame of reference for the motion of the endoscope 220 as endoscope commands. In one embodiment, a 4×4 matrix is calculated as the output of the projection. This conversion may be represented as:

$$\left[\substack{arm\\ee}\vec{O}_t, 1.0\right]^T = \substack{arm\\rcm}T_{t-1} * \left[\substack{rcm\\ee}\vec{O}_t, 1.0\right]^T \tag{8}$$

$$\substack{arm\\ee}R = \substack{arm\\rcm}R * \left(\substack{rcm\\ee}R\right)$$

$$\substack{arm\\ee}P = \begin{bmatrix} \substack{arm\\ee}R & \left(\substack{arm\\ee}\vec{O}_t\right)^T \\ 0.0, 0.0, 1.0 & 1.0 \end{bmatrix}$$

Where, $$\substack{rcm\\ee}\vec{O}_t$$

—Endoscope end position vector (1×3) in RCM frame $$\overset{arm}{\underset{ee}{\vec{O}}}_{t-1}$$

—Endoscope end position vector (1×3) in arm base frame $$\overset{rcm}{\underset{ee}{R}}$$

—Endoscope end frame rotation matrix (3×3) in RCM frame $$\overset{arm}{\underset{ee}{R}}$$

—Endoscope end frame rotation matrix (3×3) in arm base frame $$\overset{arm}{\underset{ee}{P}}$$

—pose matrix (4×4) as the final position and orientation command.

The pose (linear translation and rotational position) of the end effector is represented as a matrix with rotation and translation for the end effector on the robotic manipulator 220.

In optional act 314, the controller scales the linear translation component of the movement of the endoscope 220. To move the end effector or tip of the endoscope 220 within the patient, the robotic arm 122 moves. In addition to the amount of motion or translation of the end effector, the closeness of the end effector to the remote center of motion determines the magnitude and/or speed of motion of the robotic arm 122 outside the patient. When the endoscope tip is close to the remote center of motion, the motion of the opposite end of the arm (i.e., motion of the tool driver 210) is amplified due to the large lever about the remote center of motion, which stays stationary during teleoperation. This large lever results in excessive motion on this opposite end. The excessive motion may cause the robotic arm 122 to vibrate.

To reduce vibration, the linear component of the movement of the endoscope 220 is scaled. The linear component is reduced, such as lowering the speed of movement. In alternative or additional embodiments, the rotational components are scaled.

The scaling may be for all translation. All components of translation are scaled the same, but different scaling for different directions may be used. One use case is to only scale the x and y motion but leave the z motion (zoom in/out or movement along the view axis) unscaled, such that when the endoscope 220 is close to the remote center of motion, the zoom in/out motion is not affected. An alternative method is to scale all motions with the same scaling.

Alternatively, the scaling is for translation when the end effector is within a threshold distance of the remote center of motion. The linear motion O (x,y,z) is scaled when the endoscope end is close to the remote center of motion, such that excessive motion of the arm 122 and/or tool driver 210 is suppressed. As a result, the vibration is also suppressed. In one embodiment, the amount of the scaling is based on a distance of the endoscope from a remote center of motion of the robotic manipulator. Different distances provide for different amounts of scaling. A series of two or more threshold distances of the end effector from the remote center of motion are provided to step up the amount of scaling as the end effector approaches the remote center of motion. Alternatively, a continuous scaling with distance is provided.

In one example of this dynamic scaling, O=O*r, where r is the scaling factor. The scaling factor r is calculated as: r=1.0, when distance_to_rcm>distance_to_rcm_threashold and r=(distance_to_rcm/distance_to_rcm_threshold)$^2$, when distance_to_rcm<=distance_to_rcm_threshold. Other functions may be used to dynamically or continuously scale based on distance to the remote center of motion. The components of the O[x,y,z] vector are scaled collectively as shown above or individually scaled by r.

In act 315, the controller maps the movement of the endoscope 220 provided by the endoscope commands with or without scaling to movement of one or more joints of the robotic manipulator 122. In the example robotic manipulator 122 of FIG. 2, the motion for four or fewer joints is determined (e.g., joints J6-8 and rotation of the endoscope). The joints of the robotic manipulator 220 provide less than six degrees of freedom during teleoperation.

The controller projects from the remote center of motion frame of the robotic arm to joint position commands for the robotic arm 122. Any projection may be used, such as performing inverse kinematics. In one embodiment, the joint motions are generated or calculated by inverse kinematics (IK) using singular value decomposition. Since the six degrees of freedom motion from the user input devices (e.g., UIDs 116) as the master device has been projected into the arm workspace, the IK should always converge.

In one embodiment, the joint position command is calculated as: θ=pinv(J)*Twist, where J is the 6×4 Jacobian matrix at time t, Twist is the 6×1 vector representing the pose difference from pose at time t−1 and pose at time t, and θ is a 4×1 vector of joint position command.

The solution for joint positions (pose) or changes in joint position (pose) may be constrained. For example, a minimum distance of the end effector (e.g., tip of the endoscope 220) to the remote center of motion is enforced. The minimum distance from the endoscope end to the remote center of motion is used to prevent the endoscope 220 from being pulled out of the cannula 214 during teleoperation. The minimum distance is treated as a joint limit on the tool translate joint J8.

In act 320, the controller controls the robotic manipulator 122. The robotic arm is driven, moving the arm. The control processor drives the robotic manipulator 122 to the selected position or configuration, such as controlling based on the sensed input translation and the projected rotation about a single axis. The control processor causes movement of the robotic manipulator 122 and/or the surgical tool 220. The output movement commands for the active joints during teleoperation cause the joints to change position. The robotic manipulator 122 is moved to be in the selected configuration.

The joint commands are implemented, causing the endoscope 220 to move as intended or commanded by the user. The endoscope 220 is moved by motion of one or more of the joints. After the various projections and scaling, including the protection to the rotation about a single axis, the joints are moved to move the endoscope 220 during teleoperation. In the example robotic arm 122 of FIGS. 2 and 4, one or more of the spherical roll joint, spherical pitch a joint, tool translate joint, and tool rotation joint may be operated to provide the desired movement.

In the example with the view direction offset from the axis of the shaft (e.g., see FIG. 6 with the 30-degree offset axis), the joint motion moves the endoscope relative to the control point. The control point is provided, such that as the user rotates the endoscope 220, the image center point remains stationary.

Figure 7:
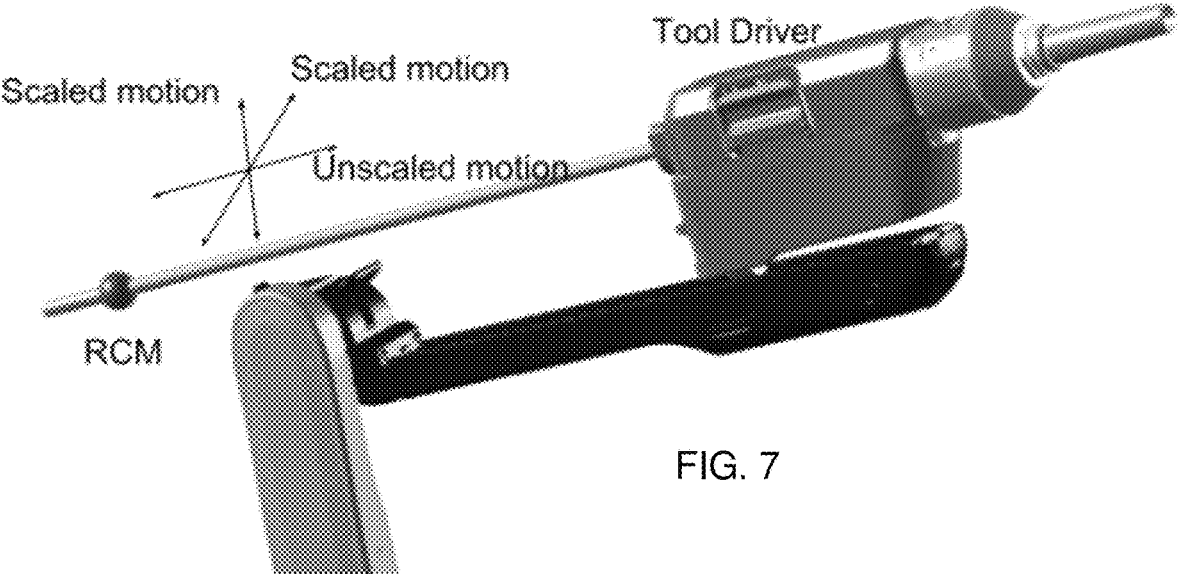
FIG. 7 illustrates an example endoscope with scaled translational motion.
Figure 8:
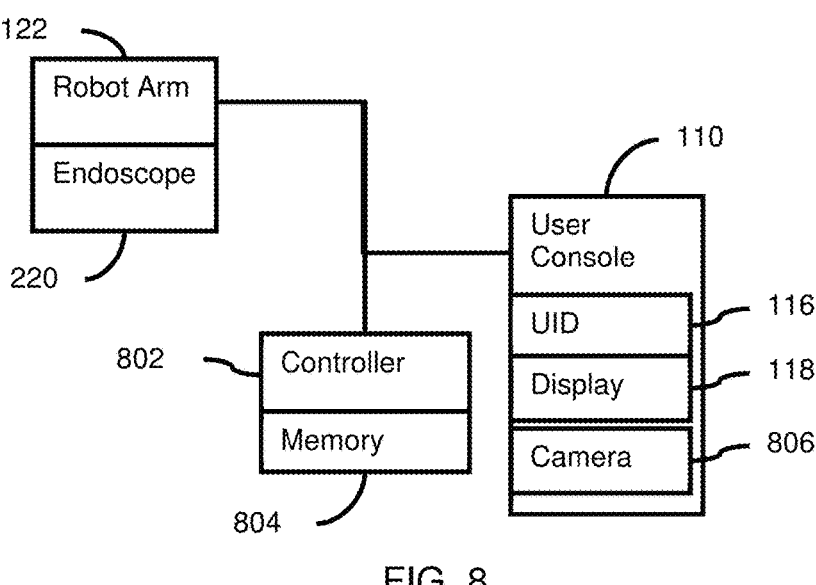
FIG. 8 is a block diagram of one embodiment of a surgical robotic system.

FIG. 7 shows a block diagram of one embodiment of a surgical robotic system for medical teleoperation. The system performs the method of FIG. 3, FIG. 5, or another method. Any one or more (e.g., all) of the projections based on sensing with untethered user interface devices having six degrees of freedom for controlling motion limited to a different number of degrees of freedom and/or constrained to the remote center of motion frame may be implemented.

The surgical robot system includes one or more robot manipulators 122 with corresponding surgical instruments a controller 802, and a memory 804. The user console 110 is represented or included as part of the surgical robot system. Additional, different, or fewer components may be provided.

The robotic manipulators 122 each include one or more links and joints. The joints may be pitch or roll joints. A tool drive 210 and cannula 214 for receiving and guiding a surgical tool may be provided on each of the robotic manipulators 122. The endoscope 220 is provided on one of the robotic manipulators 122. Different combinations of links and joints may define or form different parts of the robotic manipulators 122, such as different parts having different degrees or types of movement (e.g., translation and/or rotation). Any now known or later develop robotic manipulator 122 with motors, sensors, links, joints, controllers, surgical instruments, and/or other structure may be used.

One or more robotic manipulators 122 are provided. For example, three or four robotic manipulators 122 are provided. The robotic manipulators 122 mount to a table, such as a base of an operating table. Alternatively, cart, floor, ceiling, or other mounts may be used. The robotic manipulators 122 include a cable or wireless transceiver for communication with the controller 802 or an intermediary (e.g., control tower 130).

The robotic surgical instruments are one or more graspers, retractors, scalpels, endoscopes, staplers, scissors, or another surgical device. One surgical instrument is an endoscope 220. Different or the same type of instruments may be mounted to different ones of the robotic manipulators 122. For example, two robotic manipulators 122 may have graspers, a third robotic manipulator 122 may have a scalpel, and a fourth robot manipulator 122 may have the endoscope 220.

The robotic surgical instruments connect or are coupled to the distal ends of the robotic manipulators 122 but may connect at other locations. The connection provides a drive so that the tool may be operated, such as closing a grasper or scissors.

The endoscope 220 has an elongated shaft and a lens. The view direction of the lens is along a longitudinal axis of the shaft. The view direction may be at a non-zero angle away from the longitudinal axis, such as at 30 degrees (see FIG. 6).

The user console 110 is a graphics user interface for interaction of the surgeon with the surgical robot system, such as with a processor for controlling the robotic manipulators 122. The user interface includes one or more UIDs 116 and a display 118. The UIDs 116 and/or the display 118 are provided at the user console 110 and/or control tower 130 but may be at other locations.

The UID 116 is a handheld device. A object sized and shaped to hold in the hand or hands of the user while being free of physical connection to other devices is provided. Two handheld objects (e.g., UIDs 116) may be used, one for each hand. The two objects are free of physical connection to each other and all other devices. Alternatively, a single device for being held by both hands at a same time is provided. In yet other embodiments, one or more devices with physical connection through a cable, mechanical linkage, and/or joint are provided.

Other user inputs, such as a button, a keyboard, a rocker, a joy stick, a trackball, a voice recognition circuit, a mouse, a touch pad, a touch screen, sliders, switches, foot pedal 114, combinations thereof, or any other input device for inputting to the surgical robot may be provided. The display 118 is a monitor, liquid crystal display (LCD), projector, plasma display, CRT, printer, or other now known or later developed device for outputting visual information. In an alternative embodiment, the display 118 is a head mounted display. The user input may be a sensor or sensors for detecting eye movement and/or blinking. In yet other embodiments, the user input is a microphone for voice-based input. A speaker for output of audio information may be provided instead of or in addition to the display 118.

A base sensor senses the pose of the UIDs 116. For example, a magnetic position sensor or electric field sensor is provided. The base sensor is positioned on or near to the user console 110, such as being mounted near the display 118. In one embodiment, the optional camera 806 is the base sensor. A digital camera optically tracks user motion, such as tracking during use of the UID 116 to control the robotic manipulator 122. The camera 806 may be a stereo camera and/or depth camera in some embodiments.

The controller 802 is a controller that drives and/or models the robotic manipulators 122 and/or surgical instruments 220. The controller 802 is a general processor, central processing unit, control processor, graphics processor, graphics processing unit, digital signal processor, application specific integrated circuit, field programmable gate array, digital circuit, analog circuit, artificial intelligence processor, combinations thereof, or another now known or later developed device for controlling movement of the robot manipulator 122 and/or endoscope 220. The controller 802 is a single device or multiple devices operating in serial, parallel, or separately. The controller 802 may be a main processor of a computer, such as a laptop, server, workstation, or desktop computer, or may be a processor for handling some tasks in a larger system. Based on hardware, software, firmware, or combinations thereof, the controller 802 is configured to implement instructions or perform acts.

The controller 802 is configured to translate displacements of the one or more user interface devices to a scaled displacement the endoscope 220. The translation reduces a first degree of freedom (DoF) of rotations of the user interface devices to a fewer second DoF of rotations of the endoscope 220, such as dropping yaw and pitch in reducing from three degrees of rotation to one degree of rotation. In one embodiment, the translation includes a projection from a user motion command from the one or more UIDs 116 to an endoscope motion command, and a projection from the endoscope motion command to an arm joint motion command of the robotic manipulator 122. The reduction is performed on the user motion commands. In another embodiment, the projection from the user motion command to the endoscope motion command includes a conversion to a remote center of motion frame with the fewer second number of degrees of rotation translated to three degrees of rotation about the remote center of motion.

The memory 804 or another memory is a non-transitory computer readable storage medium storing data representing instructions executable by the programmed controller 802. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for control of an endoscope by a surgical robotic system, the method comprising:

detecting movement by a handheld user input device having six degrees of freedom;

mapping the movement by the handheld user input device to movement of the endoscope coupled to a robotic manipulator of the surgical robotic system, the mapping using projection from the six degrees of freedom of the handheld user input device limited to a fewer number of degrees of freedom of the endoscope, the projection further comprising projecting the movement by the handheld user input device from a motion command for the endoscope to a remote center of motion frame of the robotic manipulator;

calculating movements of one or more joints of the robotic manipulator to facilitate the movement of the endoscope, wherein calculating comprises projecting from the remote center of motion frame of the robotic manipulator to joint position commands for the robotic manipulator; and driving the one or more joints according to the calculated movements.

2. The method of claim 1 wherein the six degrees of freedom correspond to translations along three spatial dimensions and rotations about the three spatial dimensions, the one or more joints comprise four or fewer joints providing less than six degrees of freedom of the robotic manipulator as the fewer number, and wherein mapping the movement of the handheld user input device to the movement of the endoscope comprises projecting only in roll space without yaw and pitch.

3. The method of claim 1 wherein detecting comprises detecting the movement based on change in position and/or orientation of two handheld user interface objects, the movement being at a center between the two handheld user interface objects.

4. The method of claim 1 wherein detecting comprises detecting the movement by a base sensor where the handheld user input device comprises one or more untethered objects.

5. The method of claim 1 wherein mapping the movement by the handheld user input device to the movement of the endoscope comprises passing linear translation and projecting angular motion as a shaft rotation of the endoscope.

6. The method of claim 1 wherein mapping the movement by the handheld user input device to the movement of the endoscope comprises mapping an angular motion about an axis from the remote center of motion of the robotic manipulator to a control point based on a non-zero angle of a viewer of the endoscope.

7. The method of claim 1 wherein mapping the movement by the handheld user input device to the movement of the endoscope comprises constraining the movement of the endoscope by the remote center of motion of the robotic manipulator.

8. The method of claim 1 wherein projecting comprises removing yaw and pitch from the movement of the handheld user input device and adding yaw and pitch of the endoscope to maintain the remote center of motion.

9. The method of claim 1 further comprising scaling a linear component of the movement of the endoscope with an amount of the scaling being based on a distance of the endoscope from the remote center of motion of the robotic manipulator.

10. The method of claim 1 wherein calculating the movements of the one or more joints comprises performing inverse kinematics.

11. A method for control of an endoscope by a surgical robotic system, the method comprising:

sensing input translation and rotation about three axes in space;

projecting the input rotation about the three axes to rotation about a single axis for the endoscope mounted to a robotic arm, wherein projecting the input rotation comprises projecting from the sensing to an input motion command for the endoscope;

projecting from the input motion command for the endoscope to a remote center of motion frame of the robotic arm, and projecting from the remote center of motion frame of the robotic arm to joint position commands for the robotic arm; and controlling the robotic arm to move the endoscope based on the sensed input translation and the protected rotation about a single axis.

12. The method of claim 11 wherein sensing comprises sensing of a first handheld, physically unconnected object in a left hand of a user and sensing a second handheld, physically unconnected object in a right hand of the user, the input translation and rotation about the three axes corresponding to six degrees of freedom at a center point between the first and second handheld, physically unconnected objects.

13. The method of claim 11 wherein projecting from the input motion command for the endoscope to the remote center of motion frame comprises converting from an arm frame for the endoscope to the remote center of motion frame and converting back from the remote center of motion frame to the arm frame with added rotation from the remote center of motion frame.

\* \* \* \* \*